United States Patent [19]

Shinohara et al.

[11] Patent Number: 5,130,461
[45] Date of Patent: Jul. 14, 1992

[54] 1,3-BIS(P-HYDROXYBENZYL)-1,1,3,3-TETRAMETHYLDISILOXANE AND METHOD FOR MAKING

[75] Inventors: Toshio Shinohara, Takasaki; Makoto Satoh, Annaka, both of Japan

[73] Assignee: Shin-Etsu Chemical Company Limited, Tokyo, Japan

[21] Appl. No.: 710,478

[22] Filed: Jun. 5, 1991

[30] Foreign Application Priority Data

Jun. 6, 1990 [JP] Japan ................ 2-147987

[51] Int. Cl.⁵ .................................. C07F 7/08
[52] U.S. Cl. .................................. 556/449
[58] Field of Search ........................ 556/449

[56] References Cited

U.S. PATENT DOCUMENTS

| | | | |
|---|---|---|---|
| 3,328,450 | 6/1967 | Plueddemann | 556/449 X |
| 3,586,705 | 6/1971 | Owen et al. | 556/449 X |
| 3,697,569 | 10/1972 | Miranov et al. | 556/449 |
| 4,745,169 | 5/1988 | Sugiyama et al. | 556/449 X |
| 4,783,495 | 11/1988 | Pastor et al. | 556/449 X |

FOREIGN PATENT DOCUMENTS

| | | | |
|---|---|---|---|
| 2102811 | 8/1972 | Fed. Rep. of Germany | 556/449 |
| 1196366A | 12/1985 | U.S.S.R. | 556/449 |

*Primary Examiner*—Paul F. Shaver
*Attorney, Agent, or Firm*—Millen, White & Zelano

[57] ABSTRACT

There is provided a novel organosilicon compound, 1,3-bis(p-hydroxybenzyl)-1,1,3,3-tetramethyldisiloxane. It is prepared by silylating 1,3-bis(p-methoxybenzyl)-1,1,3,3-tetramethyldisiloxane with trimethylsilyl iodide, followed by desilylation.

7 Claims, 2 Drawing Sheets

1,3-BIS(P-HYDROXYBENZYL)-1,1,3,3-TETRAMETHYLDISILOXANE AND METHOD FOR MAKING

This invention relates to a novel compound, 1,3-bis(p-hydroxybenzyl)-1,1,3,3-tetramethyldisiloxane which is useful for modification of polyester, polyurethane and other resins.

BACKGROUND OF THE INVENTION

In the prior art, various resins such as polyester and polyurethane are often modified by incorporating silicone therein to improve their properties or to impart silicone properties to them. For the manufacture of silicone modified materials, there are known a variety of organic silicon compounds for silicone modification or introduction. There is a need for an organic silicon compound which can be reacted with polyester, polyurethane or similar resins having a carboxyl, chloroformyl or isocyanate group for silicone modification of the resins for improving their heat resistance, weathering resistance, humidity resistance, dyeability, oxygen plasma resistance and the like so that the modified resins are useful as coating materials and semiconductor fine processing materials such as photoresist.

SUMMARY OF THE INVENTION

The inventors have found that a novel compound, 1,3-bis(p-hydroxybenzyl)-1,1,3,3-tetramethyldisiloxane of the formula:

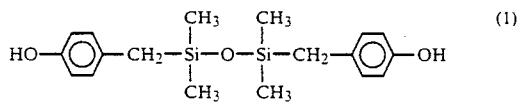

is obtained by silylating 1,3-bis(p-methoxybenzyl)-1,1,3,3-tetramethyldisiloxane of the formula:

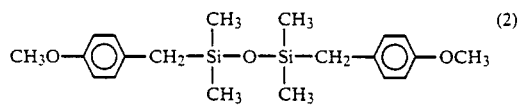

with trimethylsilyl iodide, followed by desilylation. This novel compound is useful in silicone modification.

More particularly, the organic silicon compound of formula (1) has at either end of its molecule a phenolic hydroxyl group capable of reacting with carboxyl, chloroformyl, isocyanate or other functional groups so that by reacting the compound with a polyester, polyurethane or similar resin having such a functional group, there are obtained silicone-modified resins in the form of polyester, polyurethane or similar resins having silicone incorporated therein. These silicone-modified resins are resistant against heat, weathering, humidity, oxygen plasma and the like and dyeable so that they are useful as coating materials and semiconductor fine processing materials such as photoresist.

Therefore, the present invention provides a novel organosilicon compound, 1,3-bis(p-hydroxybenzyl)-1,1,3,3-tetramethyldisiloxane of formula (1) and a method for preparing the organosilicon compound of formula (1) by silylating 1,3-bis(p-methoxybenzyl)-1,1,3,3-tetramethyldisiloxane of formula (2) with trimethylsilyl iodide, followed by desilylation.

DESCRIPTION OF THE PREFERRED EMBODIMENTS

Figure 1:
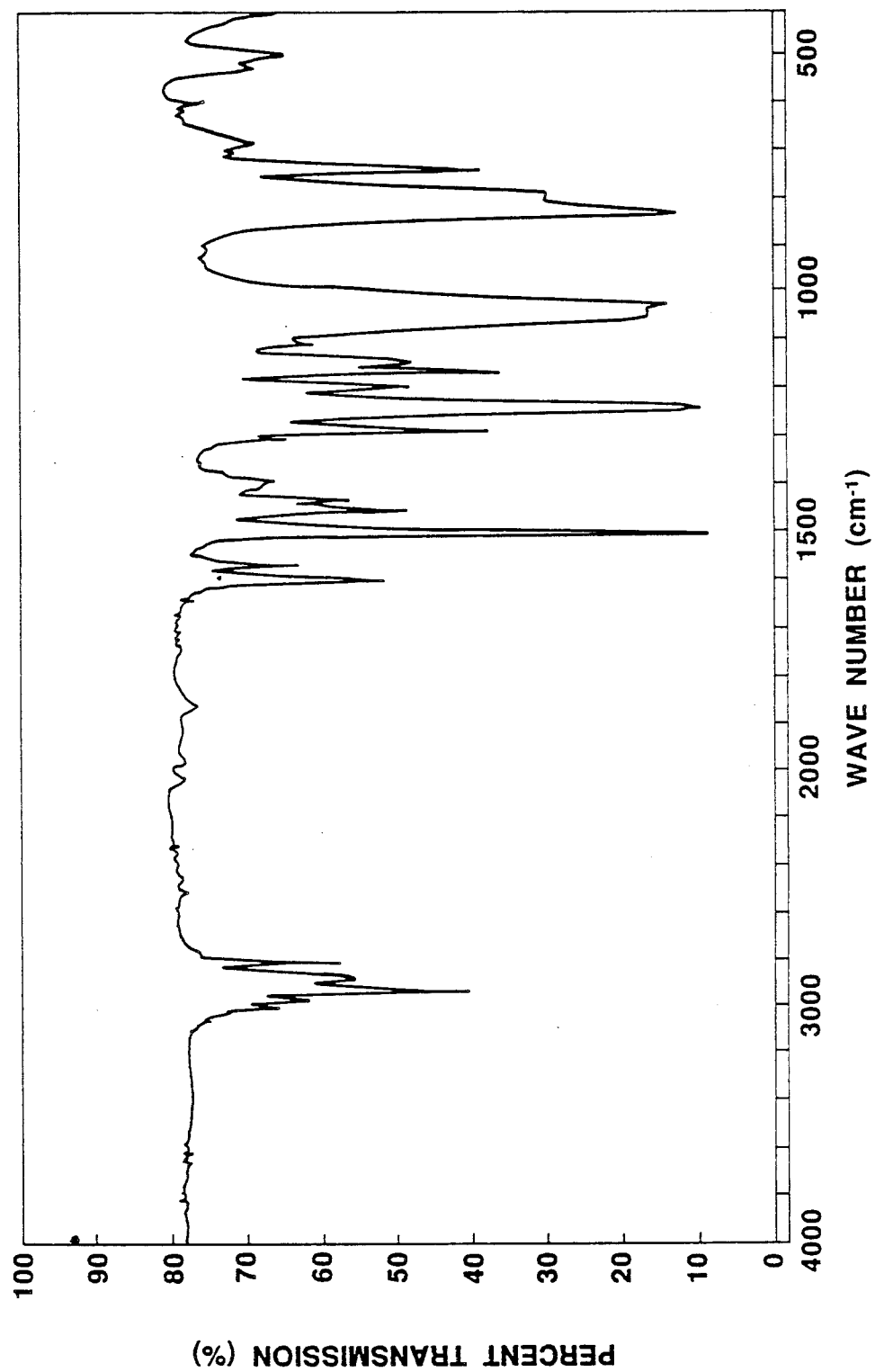
FIG. 1 is an infrared absorption spectrum of 1,3-bis(p-methoxybenzyl)-1,1,3,3-tetramethyldisiloxane.

The novel organosilicon compound of the invention is 1,3-bis(p-hydroxybenzyl)-1,1,3,3-tetramethyldisiloxane of the formula:

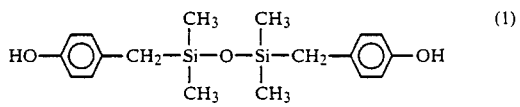

This novel organosilicon compound can be synthesized by the following method.

First, 1,3-bis(p-methoxybenzyl)-1,1,3,3-tetramethyldisiloxane of the formula:

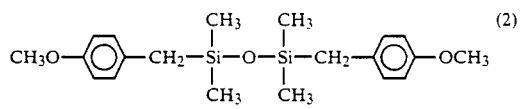

is subjected to silylation with a reactant, trimethylsilyl iodide, optionally using an inert polar solvent such as acetonitrile, carbon tetrachloride, chloroform, and dichloromethane. For silylation, the reaction temperature generally ranges from 50° to 120° C., preferably from 70° to 100° C. and the reaction time ranges from about 3 to 40 hours. Silylation proceeds as follows.

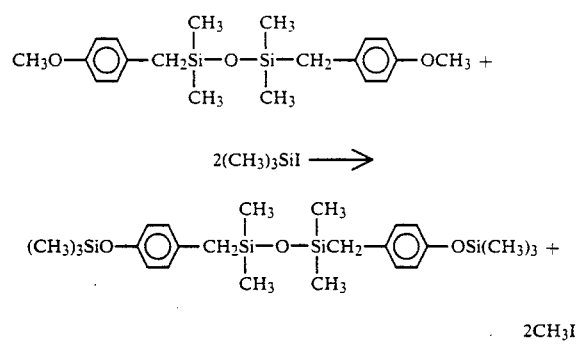

There is obtained an organosilicon compound having a trimethylsiloxy group at either end. Next, methanol or water is added to the organosilicon compound and they are mixed whereby a trimethylsilyl group is released from the benzene nucleus to leave a hydroxyl group thereat as shown in the following scheme, thus obtaining the organosilicon compound of formula (1). For this desilylation, the reaction temperature generally ranges from 40° to 120° C., preferably from 60° to 100° C. and the reaction time ranges from about 5 to 40 hours. Desilylation proceeds as follows.

-continued $$H_2O \longrightarrow$$

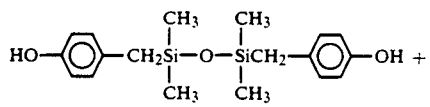
$$+ (CH_3)_3Si-O-Si(CH_3)_3$$

The starting reactant used for the preparation of the organosilicon compound of formula (1), that is, 1,3-bis(p-methoxybenzyl)-1,1,3,3-tetramethyldisiloxane of formula (2) can be synthesized by adding p-methoxybenzyltrimethoxysilane to methyl magnesium iodide (Grignard reagent) whereby reaction proceeds according to the following scheme, and effecting hydrolysis of the reaction product with the aid of hydrochloric acid or the like as also shown in the following scheme.

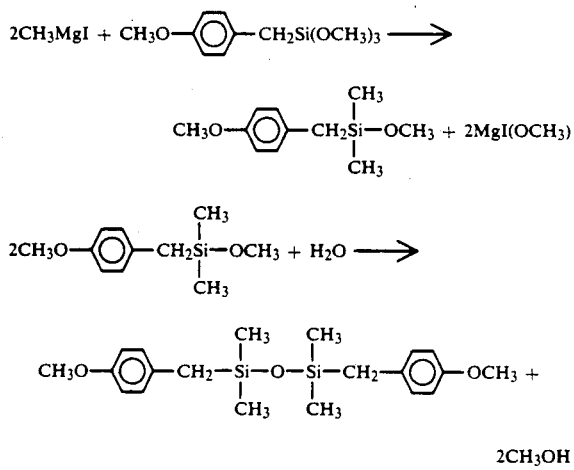

There has been described 1,3-bis(p-hydroxybenzyl)-1,1,3,3-tetramethyldisiloxane which is a novel organosilicon compound having a phenolic hydroxyl group at either end so that it can be reacted with a resin having a carboxyl, chloroformyl, isocyanate or other functional group to produce a silicone-modified resin having improved heat resistance, weathering resistance, humidity resistance, dyeability, oxygen plasma resistance and the like. This novel organosilicon compound can be efficiently synthesized by the present method.

EXAMPLE

An example of the invention is given below by way of illustration and not by way of limitation.

Synthesis of 1,3-bis(p-methoxybenzyl)-1,1,3,3-tetrametyldisiloxane

First, p-methoxybenzyltrichlorosilane was alkoxylated with methanol, obtaining p-methoxybenzyltrimethoxysilane.

The chlorosilane used for synthesis, that is, p-methoxybenzyltrichlorosilane had the following analytical data.

Boiling point: 92° C./4 mmHg

Molecular weight: 255 as measured by gas chromatography mass analysis $^1$H-NMR analysis (60 MHz, CCl$_4$, internal standard CH$_2$Cl$_2$):

δ (ppm);
2.93

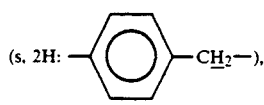
(s, 2H: —CH$_2$—), 3.83 (s, 3H: O—CH$_3$);
6.86–7.15 (m, 4H: aromatic ring)

Separately, a reactor was charged with 63 grams (2.6 mol) of magnesium fragments, and 383 grams (2.7 mol) of methyl iodide in diethyl ether was added dropwise to the reactor over 3 hours under ether reflux. Aging for a further 2 hours resulted in a Grignard reagent, methyl magnesium iodide. This reaction proceeds as follows.

$$Mg + CH_3I \rightarrow CH_3MgI$$

Next, 290 grams (1.2 mol) of p-methoxybenzyltrimethoxysilane prepared above was added dropwise to the Grignard reagent reactor at a temperature of 10° to 20° C. over one hour. After the completion of addition, the mixture was stirred for a further 2 hours at 40° C. and then 5% aqueous hydrochloric acid was added. To the organic phase was added 36% aqueous hydrochloric acid. The mixture was stirred for 5 hours at a temperature of 20° C. until hydrolysis of methoxysilane went to completion. The Grignard reaction and hydrolysis proceed as follows.

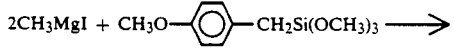

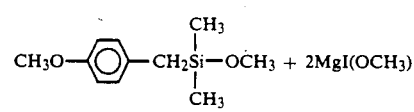

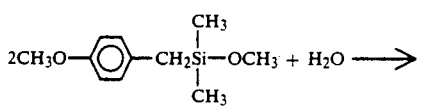

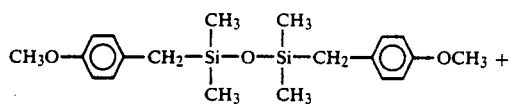

2CH$_3$OH

The organic phase was removed of low boiling fractions and then subjected to distillation under vacuum, obtaining 162 grams (0.43 mol, yield 72%) of 1,3-bis(p-methoxybenzyl)-1,1,3,3-tetramethyldisiloxane of the formula:

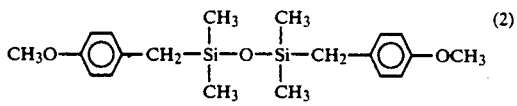
(2)

as a liquid having a boiling point of 112°–113° C./6 mmHg. Gas chromatography showed that this liquid consisted of a single component. The analytical data are shown below.

Molecular weight: 374 as measured by gas chromatography mass analysis

| Elemental analysis: | Si (%) | C (%) | H (%) |
| --- | --- | --- | --- |
| Calcd. | 14.97 | 64.17 | 8.02 |
| Found | 14.93 | 64.14 | 8.04 |

¹H-NMR analysis (60 MHz, DMSO, internal standard TMS):
δ (ppm),
−0.03 (s, 12H: Si—C$\underline{H}$₃)
1.93

(s, 4H)

3.51 (s, 6H: O—C$\underline{H}$₃);
6.56, 6.91 (m, 8H: aromatic ring) IR spectrum
The IR absorption spectrum is shown in FIG. 1.

Synthesis of
1,3-bis(p-hydroxybenzyl)-1,1,3,3-tetramethyl-disiloxane

A reactor was charged with 150 grams (0.4 mol) of 1,3-bis(p-methoxybenzyl)-1,1,3,3-tetramethyldisiloxane prepared by the above procedure and 80 grams of acetonitrile and heated to 50° C. To the reactor, 200 grams (1 mol) of trimethylsilyl iodide was added dropwise over 30 minutes. The reaction proceeds as follows.

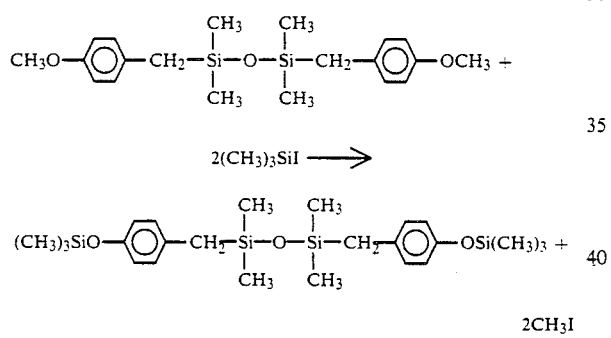

After the completion of addition, the mixture was stirred for 20 hours at 70° to 80° C. The reaction mixture was cooled to 30° C., 144 grams (8 mol) of water was added dropwise over 30 minutes, and then the mixture was stirred for 15 hours at 79° C. The reaction proceeds as follows.

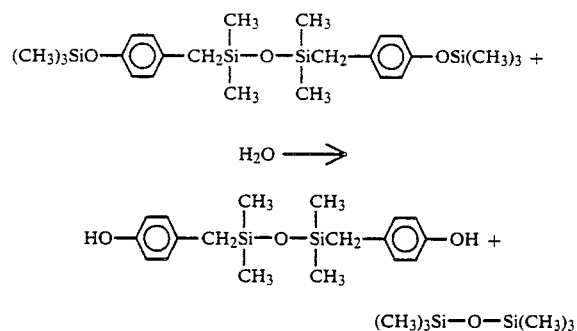

At the end of reaction, the organic and aqueous phases were separated. The organic phase was treated with an aqueous sodium thiosulfate solution to remove the coloring iodide. The decolored organic phase was further washed with water. A low boiling fraction was removed from the organic phase. The resulting viscous residue was recrystallized from ether and dried under vacuum (1 mmHg), obtaining 108 grams (0.31 mol, yield 78%) of 1,3-bis(p-hydroxybenzyl)-1,1,3,3-tetramethyl-disiloxane of the formula:

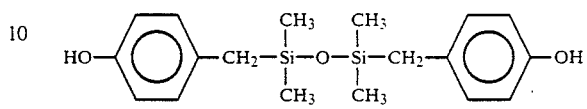

as a solid having a melting point of 66° C. Gel permeation chromatography showed that this solid consisted of a single component. The analytical data are shown below.

| Elemental analysis: | Si (%) | C (%) | H (%) |
| --- | --- | --- | --- |
| Calcd. | 16.18 | 62.43 | 7.51 |
| Found | 16.20 | 62.40 | 7.49 |

¹H-NMR analysis (60 MHz, DMSO, internal standard TMS):
δ (ppm)
−0.06 (s, 12H: Si—C$\underline{H}$₃)
1.90

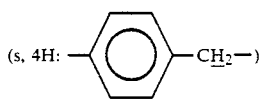
(s, 4H)

6.52–6.87 (m, 8H: aromatic ring)
8.87

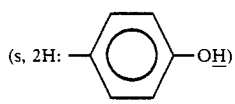
(s, 2H: O$\underline{H}$)

Figure 2:
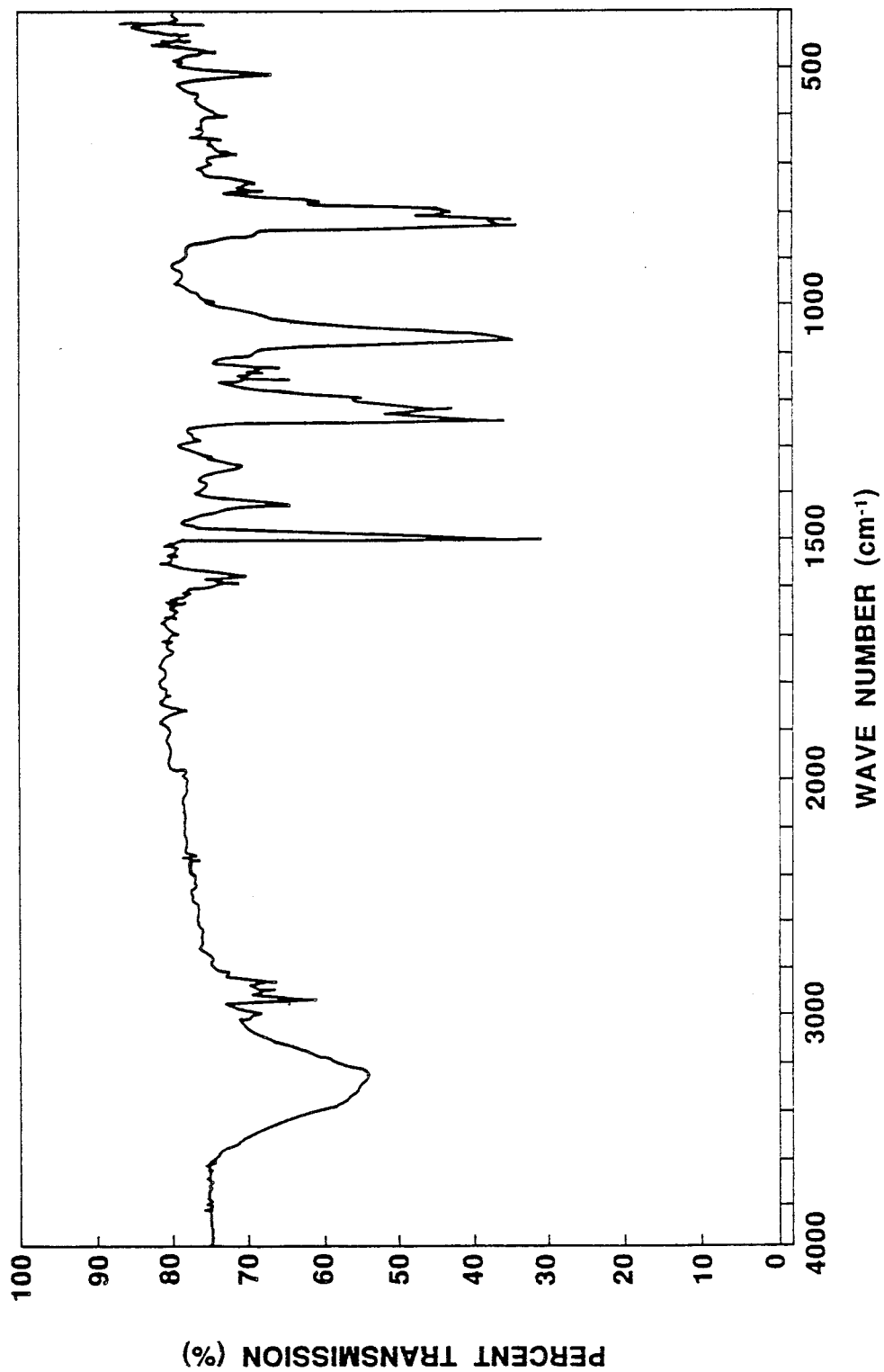
FIG. 2 is an infrared absorption spectrum of 1,3-bis(p-hydroxybenzyl)-1,1,3,3-tetramethyldisiloxane.

IR spectrum
The IR absorption spectrum is shown in FIG. 2.

We claim:
1. 1,3-bis(p-hydroxybenzyl)-1,1,3,3-tetramethyl-disiloxane of the formula:

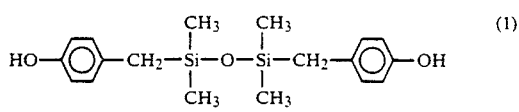
(1)

2. A method for preparing 1,3-bis(p-hydroxybenzyl)-1,1,3,3-tetramethyldisiloxane of the formula:

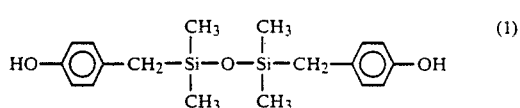
(1)

comprising the steps of silylating 1,3-bis(p-methoxybenzyl)-1,1,3,3-tetramethyldisiloxane of the formula:

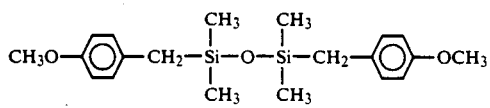 (2)

with trimethylsilyl iodide, followed by desilylation.

3. A method according to claim 2, wherein silylation reaction temperature is 70° C. to 100° C. and the reaction time is 3 to 40 hours.

4. A method according to claim 2, wherein the desilylation reaction temperature is 60° C. to 100° C. and the reaction is 5 to 40 hours.

5. A method according to claim 2, wherein the silylating agent is trimethylsilyl iodide.

6. A method according to claim 2, wherein the silylation is conducted in the presence of an inert polar solvent selected from acetonitrile, carbon tetrachloride, chloroform and dichloromethane.

7. A method according to claim 2, wherein methanol or water is added during the desilylation step.

* * * * *